United States Patent
Rössling et al.

(10) Patent No.: US 6,572,894 B2
(45) Date of Patent: *Jun. 3, 2003

(54) PROCESS FOR THE PRODUCTION OF MORPHOLOGICALLY UNIFORM MICROCAPSULES AND MICROCAPSULES THAT ARE PRODUCED ACCORDING TO THIS PROCESS

(75) Inventors: Georg Rössling, Berlin (DE); Celal Albayrak, Berlin (DE); Johannes Tack, Berlin (DE); Reinhard Schmitz, Berlin (DE)

(73) Assignee: Actipac Biosystems GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/886,504

(22) Filed: Jun. 21, 2001

(65) Prior Publication Data

US 2001/0033868 A1 Oct. 25, 2001

Related U.S. Application Data

(63) Continuation of application No. 09/068,471, filed as application No. PCT/EP96/04701 on Oct. 30, 1996, now Pat. No. 6,294,204.

(30) Foreign Application Priority Data

Nov. 24, 1995 (DE) .......................... 195 45 257

(51) Int. Cl.$^7$ .................... A61K 9/48; A61K 9/14; A61K 9/16; A61K 38/00; A01N 37/18

(52) U.S. Cl. .................. 424/497; 424/451; 424/489; 514/2; 514/937

(58) Field of Search ................. 424/497, 490, 424/489; 514/800, 2

(56) References Cited

U.S. PATENT DOCUMENTS

| 3,523,906 A | 8/1970 | Vrancken et al. |
| 3,691,090 A | 9/1972 | Kitajima et al. |
| 3,737,337 A | 6/1973 | Schnoring et al. |

(List continued on next page.)

FOREIGN PATENT DOCUMENTS

| CA | 2009941 | 8/1990 |
| CA | 2100925 | 1/1994 |
| EP | 202065 | 5/1986 |

(List continued on next page.)

OTHER PUBLICATIONS

US 5,849,884, 12/1998, Woiszwillo et al. (withdrawn)
Phillips et al. Evaluation of the Anaphylactoid Activity of a New LHRH Antagonist, Life Sciences 43;883–888, 1988.*

(List continued on next page.)

Primary Examiner—Thurman K. Page
Assistant Examiner—Todd D Ware
(74) Attorney, Agent, or Firm—Michael J. Rafa; Felissa H. Cagan

(57) ABSTRACT

The invention relates to a process for the production of morphologically uniform microcapsules that contain peptides, proteins or other water-soluble biologically active substances as active ingredients as well as microcapsules that are produced according to this process with a degree of concentration of between 3 to 30% by weight and a diameter $\leq 8\,\mu m$. According to the invention, biodegradable polymers are dissolved in a halogen-free solvent or solvent mixture, and the buffered active ingredient solution, which has a pH of between 6.0 to 8.0, is dispersed into this solution. Then, an aqueous solution that contains a surfactant (W/O/W-emulsion) is added to this W/O-emulsion, and the solvent is removed. The microcapsules that are produced with this process do not show any tendency toward agglomeration. The encapsulation efficiency of the process is approximately 90 to 95%.

14 Claims, 3 Drawing Sheets

DesANal(2)

D-Cit

U.S. PATENT DOCUMENTS

| | | |
|---|---|---|
| 3,891,570 A | 6/1975 | Fukushim et al. |
| 3,943,063 A | 3/1976 | Morishita et al. |
| 3,960,757 A | 6/1976 | Morishita et al. |
| 4,166,800 A | 9/1979 | Fong |
| 4,384,975 A | 5/1983 | Fong |
| 4,389,330 A | 6/1983 | Tice et al. |
| 4,568,559 A | 2/1986 | Nuwayser et al. |
| 4,652,441 A | 3/1987 | Okada et al. |
| 4,675,189 A | 6/1987 | Kent et al. |
| 4,732,763 A | 3/1988 | Beck et al. |
| 4,835,139 A | 5/1989 | Tice et al. |
| 4,897,268 A | 1/1990 | Tice et al. |
| 4,917,893 A | 4/1990 | Okada et al. |
| 4,954,298 A | 9/1990 | Yamamoto et al. |
| 4,962,091 A | 10/1990 | Eppstein et al. |
| 4,994,281 A | 2/1991 | Muranishi et al. |
| 5,019,400 A | 5/1991 | Gombotz et al. |
| 5,271,961 A | 12/1993 | Mathiowitz et al. |
| 5,330,767 A * | 7/1994 | Yamamoto et al. ......... 424/497 |
| 5,366,734 A | 11/1994 | Hutchinson |
| 5,384,133 A | 1/1995 | Boyes et al. |
| 5,445,832 A | 8/1995 | Orsolini et al. |
| 5,500,161 A | 3/1996 | Andrianov et al. |
| 5,503,851 A | 4/1996 | Mank et al. |
| 5,536,508 A | 7/1996 | Canal et al. |
| 5,556,642 A | 9/1996 | Kobayashi et al. |
| 5,594,091 A | 1/1997 | Igari et al. |
| 5,603,960 A | 2/1997 | O'Hagen et al. |
| 5,609,886 A | 3/1997 | Wantier et al. |
| 5,611,971 A | 3/1997 | Maedera et al. |
| 5,622,657 A | 4/1997 | Takada et al. |
| 5,631,020 A | 5/1997 | Okada et al. |
| 5,631,021 A | 5/1997 | Okada et al. |
| 5,635,216 A | 6/1997 | Thompson |
| 5,643,605 A | 7/1997 | Cleland et al. |
| 5,648,095 A | 7/1997 | Illum et al. |
| 5,648,096 A | 7/1997 | Gander et al. |
| 5,650,173 A | 7/1997 | Ramstack et al. |
| 5,661,125 A | 8/1997 | Strickland |
| 5,676,968 A | 10/1997 | Lipp et al. |
| 5,700,486 A | 12/1997 | Canal et al. |
| 5,723,269 A | 3/1998 | Akagi et al. |
| 5,733,567 A | 3/1998 | Arola et al. |
| 5,766,637 A | 6/1998 | Shine et al. |
| 5,783,567 A | 7/1998 | Hedley et al. |
| 5,792,477 A | 8/1998 | Rickey et al. |
| 5,851,451 A | 12/1998 | Takechi et al. |
| 5,853,698 A | 12/1998 | Straub et al. |
| 5,863,554 A | 1/1999 | Illhun |
| 5,902,565 A | 5/1999 | Cox et al. |
| 5,902,834 A | 5/1999 | Porrvik et al. |
| 5,916,598 A | 6/1999 | Rickey et al. |
| 5,922,357 A | 7/1999 | Coombes et al. |
| 5,929,196 A | 7/1999 | Kissel et al. |
| 5,955,143 A | 9/1999 | Wheatley et al. |
| 5,980,947 A | 11/1999 | Yamakawa et al. |
| 5,981,474 A | 11/1999 | Manning et al. |
| 5,985,312 A | 11/1999 | Jacob et al. |
| 5,993,855 A | 11/1999 | Yoshimoto et al. |
| 6,007,845 A | 12/1999 | Domb et al. |
| 6,020,004 A | 2/2000 | Shah |
| 6,048,551 A | 4/2000 | Hilfinger et al. |
| 6,080,429 A | 6/2000 | Cleland et al. |
| 6,110,503 A | 8/2000 | Rickey et al. |
| 6,113,943 A | 9/2000 | Okada et al. |
| 6,120,805 A | 9/2000 | Spenlchauer et al. |
| 6,143,211 A | 11/2000 | Mathiowitz et al. |
| 6,290,983 B1 | 9/2001 | Rickey et al. |
| 6,291,013 B1 | 9/2001 | Gibson et al. |

FOREIGN PATENT DOCUMENTS

| | | |
|---|---|---|
| EP | 251476 | 5/1986 |
| EP | 190833 | 8/1986 |
| EP | 302582 | 3/1987 |
| EP | 330180 | 2/1989 |
| EP | 0315875 | 5/1989 |
| EP | 438426 | 9/1989 |
| EP | 580428 | 7/1993 |
| EP | 582459 | 8/1993 |
| EP | 797615 | 3/1995 |
| EP | 04481732 | 3/1995 |
| EP | 0668073 | 4/1999 |
| GB | 1405108 | 12/1971 |
| GB | 2234896 | 2/1991 |
| WO | 90/13780 | 11/1990 |
| WO | 97/19676 | 6/1997 |
| WO | 98/07442 | 2/1998 |
| WO | 98/27962 | 7/1998 |
| WO | WO 99/20253 | 4/1999 |
| WO | WO 99/29304 | 6/1999 |
| WO | WO 00/04916 | 7/1999 |
| WO | WO 99/58112 | 11/1999 |
| WO | WO 99/59548 | 11/1999 |
| WO | WO 01/28591 | 4/2001 |

OTHER PUBLICATIONS

Arshady, "Preparation of biodegradable microspheres and microcapsules: 2. Polyactides and related polyesters," J. of Cont. Rel., 17th ed., pp. 1–22, (Feb. 5, 1991).

Watts et al., "Microencapsulation Using Emulsification/ Solvent Evaporation: An Overview of Techniques and Applications," Critical Reviews in Therapeutic Drug Carrier Systems, vol. 7 (No. 3), pp. 235–259, (Feb. 5, 1990).

Wang et al., "Preparation and Characterization of Poly(lactic–co–glycolic acid) Microspheres for Targeted Delivery of a Novel Anticancer Agent, Taxol," Chem. Pharm. Bull., Pharmaceutical Society of Japan, vol. 44 (No. 10), pp. 1935–1940, (Oct. 1, 1996).

Ghaderi et al., "Effect of preparative parameters on the characteristics of poly (D.L–lactide–co–glycolide) microspheres made by the double emulsion method," International Journal of Pharmaceutics, Elsevier Science B.V., pp. 205–216, (Jun. 16, 1996).

Cleland, "Solvent evaporation processes for the Production of Controlled Release Biodegradable Microsphere Formulations for Therapeutics and Vaccines," Biotechnol. Prog., 1st ed., American Chemical Society & American Institute of Chemical Engineers, vol. 14 (No. 1), pp. 102–107, (Feb. 6, 1998).

O'Donnell et al., "Properties of multiphase microspheres of poly(dl–lactic acid) or poly(dl–lactic–co–glycolic acid) produced by mechanical agitation, sonication, or potentiometric dispersion," J. Microencapsulation, Taylor & Francis Ltd., vol. 13 (No. 6), pp. 667–677, (Feb. 5, 1996).

Carti, "A new approach to imporved stability and controlled release in double emulsions, by the use of graft–comb polymeric amphiphiles," Acta Polym, Wiley–VCH (Weinhelm), p. 606–616, (Feb. 5, 1998).

Aftabroushad et al., "Factors Influencing the Entrapment of a Water Soluble Model Drug into Injectable Microparticles Prepared Using Solvent Evaporation and Phase Seperation Techniques," Eur. J. Pharm BioPharm, medpharm GmbH Scientific Publishers (Stuttgart), vol. 40 (No. 4), pp. 237–242, (Feb. 5, 1994).

* cited by examiner

DesANal(2)　　　　　　　　　D-Cit

DesA(2)Nal-beta Ala-DCpa-DPal-Ser-Tyr-DCit-Leu-Arg-

DesA(2)Nal-Gly-DCpa-DPal-Ser-Tyr-DCit-Leu-Arg-Pro-DAla-NH$_2$

Ac-DNal-DCpa-DPal-Ser-Tyr-DLys(Mor)-Leu-Lys(Mor)-Pro-DAla-NH$_2$

PROCESS FOR THE PRODUCTION OF MORPHOLOGICALLY UNIFORM MICROCAPSULES AND MICROCAPSULES THAT ARE PRODUCED ACCORDING TO THIS PROCESS

The present application is a continuation of U.S. patent application Ser. No. 09/068,471, filed Sep. 25, 1998, now U.S. Pat. No. 6,294,204 which is a 371 of PCT/EP96/04701, filed Oct. 30, 1996, which claims priority to German application 195 45 257.7 filed Nov. 24, 1995.

FIELD OF THE INVENTION

The invention relates to a process for the production of morphologically uniform microcapsules that contain peptides, proteins, or other water-soluble biologically active substances as active ingredients, and microcapsules that are produced according to this process.

BACKGROUND OF THE INVENTION

As is generally known, peptides and proteins represent active ingredients with sizeable pharmacodynamics, which, however, are broken down upon oral administration because of their hydrolysis sensitivity in the acidic environment of the stomach, as well as enzymatic degradation, and thus are partially inactivated in such a way that their action in the gastrointestinal tract is considerably reduced.

Rapid inactivation of proteins and peptides can be observed, however, even after parenteral administration and especially after intravenous administration because of the half-life, which is very often very short. This means that despite sizeable pharmacodynamics and theoretically lower therapeutic dosages, multiple administrations of higher dosages may be necessary, which mean a large burden on the patients.

Suitable formulations that avoid the above-mentioned drawbacks are depot systems in the form of polymer microcapsules or polymer nanocapsules, which are also known extensively for peptides and are described in the literature.

They have the advantages that

Peptides and proteins are protected against rapid inactivation, lower dosages are pharmacologically effective, multiple administration can be reduced, controlled release of peptides and proteins is possible in principle, the encapsulated active ingredients are transported in a directed manner, and undesirable side-effects can be reduced.

The known processes for microencapsulation or nanoencapsulation of water-soluble substances can be divided as follows:

Coacervation or emulsion phase separation encapsulation by spray drying solvent-evaporation in an organic or aqueous phase.

All processes include the embedding of active ingredients into a biodegradable polymer matrix or copolymer matrix.

Polymers that are known from the literature for this purpose are polyamides, polyanhydrides, polyesters, polyorthoesters, polyacetates, polylactones, polyorthocarbonates, i.a. To date, polylactide-co-glycolide polymers have mainly been used.

Thus, pharmaceutical compositions of water-soluble peptides and proteins in capsule form, which were produced based on coacervation or emulsion phase separation, are known from, e.g., U.S. Pat. No. 4,675,189 (Syntex Inc.), U.S. Pat. No. 4,835,139 (Debiopharm S.A.) and EP 302 582 B1 (Southern Research Inst.).

According to this disclosure, processes are described in which the copolymer that is used, preferably poly-(lactide-co-glycolide)-polymer, is dissolved in a halogenated organic solvent, preferably dichloromethane, and an aqueous peptide solution is dispersed in this solution. Then, a so-called coacervation agent is added. The coacervation agent is soluble in the organic solvent, but the polymer is insoluble in the coacervation agent, causing precipitation of the polymer with the inclusion of the dispersed polypeptides. As a coacervation agent, usually silicone oil is used for phase separation. After the silicone oil is added, a large amount of heptane, which ensures the setting of the microcapsules, must be added as well.

The encapsulation efficiency of this method is approximately 70% (U.S. Pat. No. 4,835,136). The microcapsules that are produced have a diameter of 1 to 500 $\mu$m, preferably 10 to 50 $\mu$m according to the examples.

In addition to the use of toxicologically problematic agents such as dichloromethane, heptane, and silicone oil, the drawbacks of this process also include the need to use large amounts of solvent, which results from the encapsulation using coacervation agents, such as silicone oil.

A process that is described in EP-A 315875 (Hoechst AG) for the production of biodegradable microcapsules of water-soluble peptides and proteins is based on the spray-drying process, in which an aqueous peptide or protein solution is emulsified in an organic polymer solution, and this emulsion is spray-dried.

As a biodegradable polymer, a mixture of polyhydroxybutyric acid and poly (lactide-co-glycolide) polymer is used in a mixing ratio of between 99:1 to 20:80.

The peptide or protein is present in micronized form or in an aqueous solution. As a solvent, chloroform, dichloromethane, DMF or a solvent mixture that consists of water/ethanol/chloroform are considered. According to the examples, chloroform is used. The spray drying is carried out at temperatures of between preferably 45 and 95° C.

Disadvantageous in this process is the potential risk of explosion when a non-halogenated solvent is used and high temperatures are used simultaneously during the drying process. Moreover, the use of non-flammable solvents such as dichloroethane results in toxicologically harmful residual solvent contamination in the end product. In addition, spray-dried microcapsules basically show a strong tendency to agglomerate; agglomerates of about 100 $\mu$m in size are produced.

Microparticles that are produced according to the "solvent-evaporation-process" are described in two Canadian Patent Applications CA 2,100,925 (Rhone-Merieux) and CA 2,099,941 (Tanabe Seiyaku Co.).

Usually, with this method, the aqueous peptide or protein solution is dispersed into an organic polymer solution, or active ingredient crystals are suspended in the polymer solution. After a second aqueous phase is added with a surfactant, the polymer solvent is evaporated.

This method is highly variable, and normally W/O— or complex W/O/W-emulsions are produced.

According to CA 2,099,941, water-soluble active ingredients and biodegradable polymers are first dissolved in a solvent or a solvent mixture in which they are both soluble. Then, this solvent is removed, and the solid dispersion that is produced is dissolved in an organic solvent that is not water-miscible. The resulting solution (oil phase) is emulsified in an aqueous phase, so that a W/O-emulsion is produced.

Finally, the organic solvent of the oil phase of this emulsion is evaporated.

Concrete examples of the patent relate to poly (lactide-co-glycolide) polymers (PLGA) as a matrix and a hormone (TRH) that releases thyreotropin or its derivatives as an active ingredient, which are first dissolved in a mixture that consists of acetonitrile/ethanol and optionally water, or only acetonitrile, or that consists of acetonitrile and aqueous gelatin, or of dichloromethane and ethanol.

As an organic solvent in the solution of the solid dispersion, dichloromethane or chloroform is used. An aqueous polyvinyl alcohol solution represents the aqueous phase.

The size of the microcapsules is approximately a diameter of 1 to 100 µm, according to the concrete examples about 50 µm to <100 µm.

According to CA 2,100,925, microcapsules of LHRH hormone and analogs are produced by prior dispersion of the LHRH hormone in powder form in two organic solvents, whereby one solvent (above-mentioned dispersion solvent) makes it possible to produce a homogeneous suspension of the pulverized hormone by simple stirring. The second solvent is readily water-miscible and thus makes the micro-dispersion of the organic phase in aqueous phase possible.

As a second solvent, dichloromethane or, alternatively, chloroform is used. The capsules have a diameter of between 1 and 250 µm. Preferably, the capsules are larger than 50–60 µm.

The morphology of the microcapsules that are thus produced is also very different. As already explained above, the halogenated solvents that are used are toxicologically harmful. In addition, this process also requires sizeable amounts of surfactants.

SUMMARY OF THE INVENTION

The object of the invention was to develop a simple and gentle process for the production of morphologically uniform, non-agglomerating microcapsules using toxicologically harmless solvents, which have an encapsulation efficiency of at least 85%, preferably over 90%, and is to yield microcapsules in a size range of 200 nm to 500 µm with a high degree of concentration. In addition, the process is to make "scaling-up" possible.

DETAILED DESCRIPTION OF THE INVENTION

Figure 1:
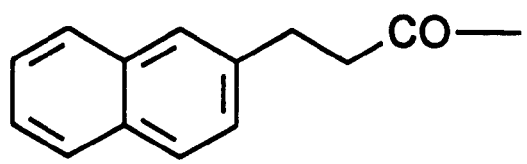
FIG. 1 depicts the chemical structures of DesA(2)Nal and D-Cit.
Figure 1:
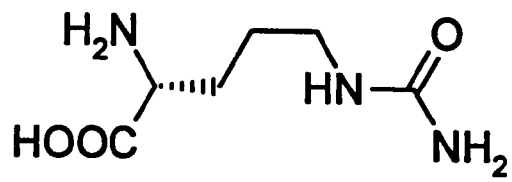

The object of the invention is achieved surprisingly simply using the "Induced Phase Transition" method, which is implemented by virtue of the fact that a polymer that is commonly used for microcapsule production, such as a polyester that consists of hydroxycarboxylic acids or a block polymer that consists of hydroxycarboxylic acids and polyethylene glycol (PEG), is dissolved in a halogen-free, solvent or solvent mixture that is not water-miscible or is partially water-miscible and the buffered active ingredient solution, which has a pH of between 6.0–8.0, is dispersed in this solution. Homogenization produces a stable W/O-emulsion to which an aqueous solution that contains a surfactant or a mixture of surfactants is added as an outer phase while being stirred, in such a way that a three-phase W/O/W emulsion is obtained. Then, the solvent or solvent mixture is removed with commonly used methods, preferably in a vacuum and/or air/nitrogen stream. The microcapsules are concentrated and optionally freeze-dried.

In this case, the particle size is controlled by the stirring speed, whereby smaller particles ($\leq 8$ µm)—such as are required if the product is intended for intravenous administration—are obtained at higher stirring speeds.

Optionally, after the solvent is removed, the microcapsules are additionally subjected to "cross-flow" filtration, by which residual surfactant and residual solvent portions are removed. As a result, it is possible to reduce or to avoid the "initial burst," i.e., a large release of active ingredients immediately after administration (because of active ingredients that adhere to the particle surface).

For freeze-drying, cryoprotectors such as sugar, sugar alcohols, or polyvinylpyrrolidone derivatives are optionally added.

Preferred polyesters of hydroxycarboxylic acids that can be used in the process according to the invention are:

Polyglycolides (PGA) and copolymers of glycolides, such as glycolide/lactide copolymers (PGA/PLLA) or glycolide/trimethylene carbonate copolymers (PGA/TMC); L-polylactides (PLA) and stereocopolymers of polylactides such as poly-L-lactide (PLLA), poly-DL-lactide copolymers and L-lactide/DL-lactide copolymers; copolymers of PLA such as lactide/tetramethylglycolide copolymers, lactide/δ-valerolactone copolymer and lactide/ξ-caprolactone copolymer; poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolactone, hydrophobized polysaccharides, hyaluronic acid, dextrans or hydrophobized amylopectin and poly-ξ-caprolactone.

As block copolymers of polyesters of hydroxycarboxylic acids and linear or star-polyethylene glycol (PEG), the substances named below can be used in the process according to the invention:

AB-block copolymers that consist of PLA and PEG, ABA-triblock copolymers that consist of PLA-PEG-PLA, S(3)-PEG-PLA block copolymers and S(4)-PEG-PLA block copolymers.

The polymer Resomer® 505, especially Resomer® RG-756 or Resomer® RG-858, is preferred according to the invention.

Resomer® is a trademark of the Böhringer Ingelheim Company. In this case, this is a (DL-lactide-co-glycolide)-polymer.

Halogen-free solvents or solvent mixtures that are preferred according to the invention are acetone, ethanol, alkyl acetates such as methyl, ethyl, propyl, isopropyl or butyl acetate, alkyl formates such as methyl-, ethyl-, propyl-, isopropyl- or butyl formate, triacetin, triethyl citrate and/or $C_1$–$C_4$ alkyl lactates, e.g., methyl or ethyl lactate.

Ethyl acetate, isopropyl acetate, and propyl formate are especially preferably used.

For the purposes of this invention, buffered solutions are aqueous solutions of peptides, proteins or their physiologically compatible salts or of other water-soluble biologically active substances, which are preferably adjusted with a tris (hydroxymethyl) aminomethane solution or a phosphate buffer solution to a pH of between 6.0 and 8.0, preferably a pH of 6.5 to 7.4.

Another buffer that can be used according to the invention is the citrate buffer, whereby the buffer concentrations are generally in the range of 5 mmol/l to 300 mmol/l.

Any water-soluble peptides or proteins can be encapsulated with the process according to the invention. The process according to the invention is especially suitable for encapsulating human serum albumin, insulin, interferon, and LHRH antagonists or their analogs.

Morphologically uniform microcapsules of human serum albumin, insulin, interferons, and the peptides that are mentioned below can quite especially advantageously be produced with the process according to the invention:

a) DesA(2)Nal-beta-Ala-DCpa-DPal-Ser-Tyr-DCit-Leu-Arg-Pro-DAla-NH$_2$,
b) DesA(2)Nal-Gly-DCpa-DPal-Ser-Tyr-DCit-Leu-Arg-Pro-DAla-NH$_2$,
c) Ac-DNal-DCpa-DPal-Ser-Tyr-DLys(Mor)-Leu-Lys(Mor)Pro-DAla-NH$_2$.

Figure 2A:
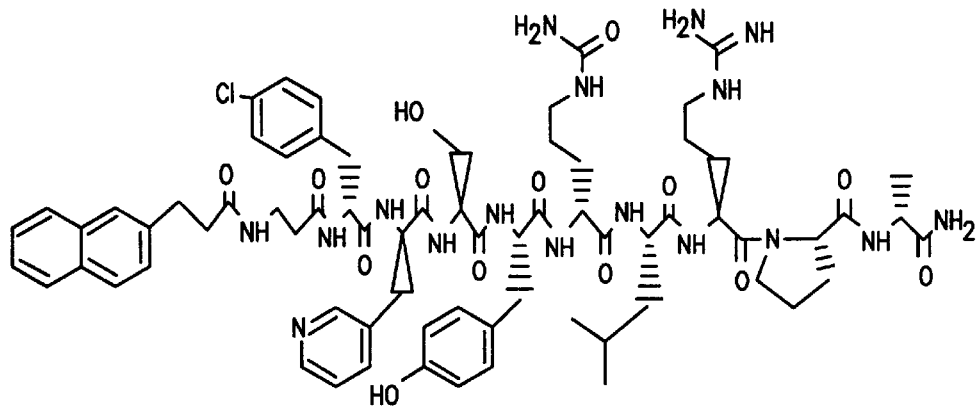
FIGS. 2a–2c depict the chemical structures of exemplary peptides that can be used with the process of the present invention.
Figure 2B:
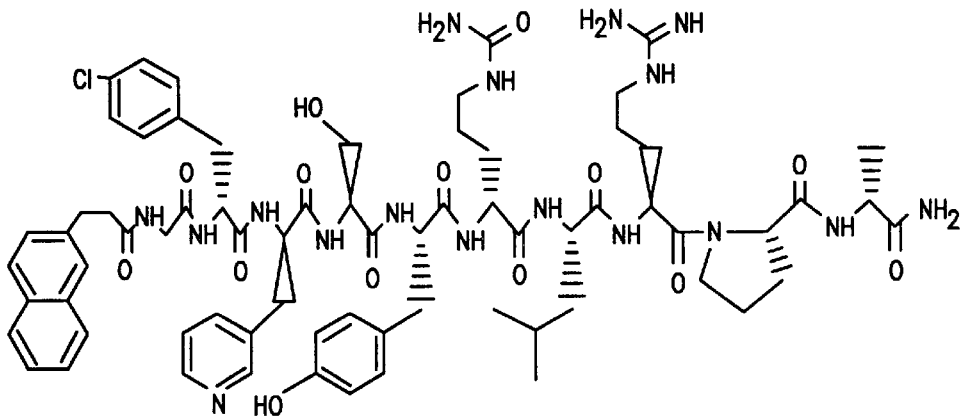
Figure 2C:
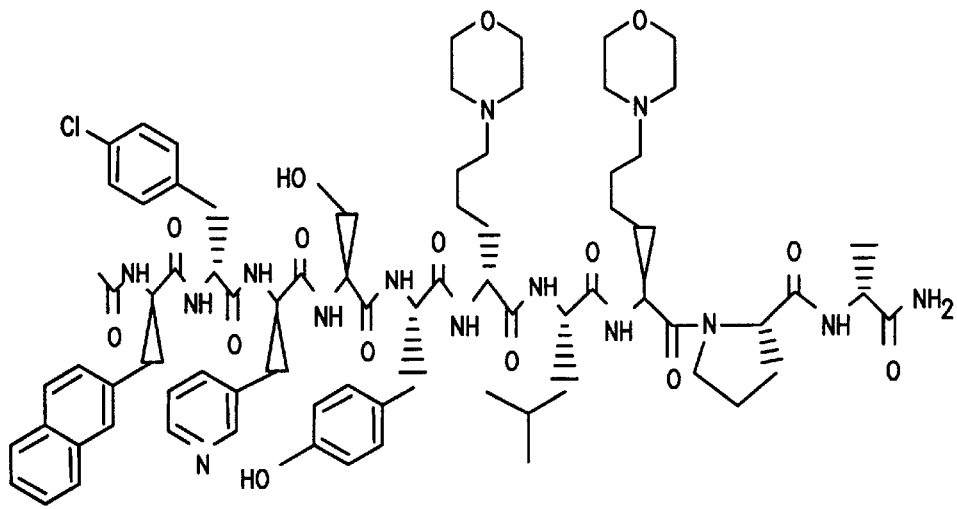

The meanings of DesA(2)Nal and D-Cit and the chemical structures of peptides a) to c) are presented in FIG. 1 or 2.

For the purposes of the invention, preferred as surfactants are substances from the Poloxamere® group, polyethylene glycol alkyl ethers, polysorbates (Tween®, Span®), saccharose esters (Sisterna®, The Netherlands), saccharose esters (Ryoto sugar esters, Tokyo), gelatin, polyvinylpyrrolidone, fatty alcohol polyglycoside, charps, charpso, decyl-β-D-glycopyranoside, decyl-β-D-maltopyranoside, dodecyl-β-D-maltopyranoside, sodium-oleate, Poloxamine® group, polyethylene glycol, polyvinyl alcohol, polyoxyethylated fatty acid ether (Brij®) Triton X 100 or mixtures thereof.

Polyvinyl alcohol, Brij®, Poloxamere® Poloxamine® and Tween® are preferably used.

The subject of the invention is also morphologically uniform microcapsules that are produced according to the above-mentioned process and have a diameter of 200 nm to 500 μm, preferably between 0.2 to 8 μm.

Because of the advantageous conformation of polymer and solvent, no formation of agglomerates of the microcapsules occurs in the process according to the invention.

Figure 3:
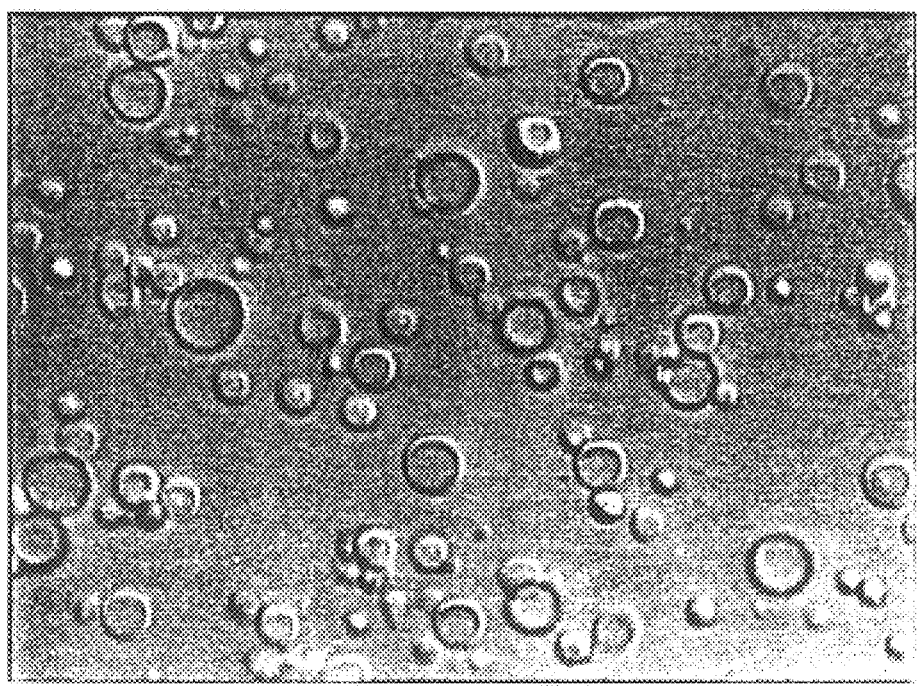
FIG. 3 is light-microscopic image of microcapsules produced according to Example 10.
Figure 4:
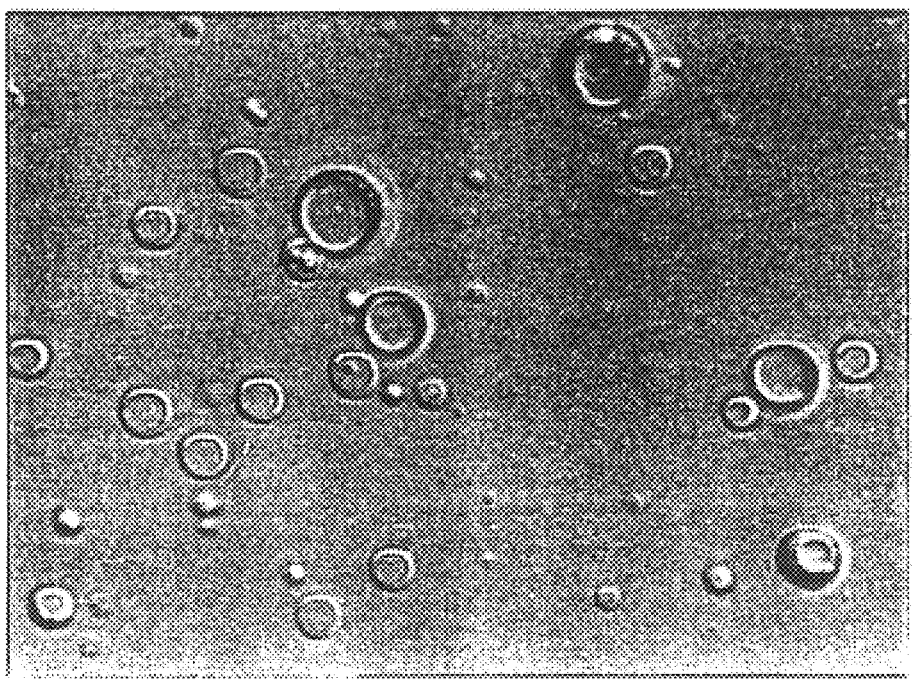
FIG. 4 is a light-microscopic image of microcapsules produced according to Example 15.

Thus, FIGS. 3 and 4 show light-microscopic pictures of the microcapsules according to the invention that are produced according to Example 10 (FIG. 3) or according to Example 15 (FIG. 4). A millimeter in the imaging corresponds to 1 μm in reality. The pictures clearly show the uniform morphology; particle agglomerates are not present.

The encapsulation efficiency of the process is at least 85%; preferably encapsulation efficiencies of between 90 and 95% are achieved. The mass of the encapsulated active ingredient·100/mass of the active ingredient that is used is defined as encapsulation efficiency. The degree of concentration of the microcapsules that are produced is between concentration=mass of active ingredient·100/mass of active ingredient+mass of polymer).

Then, the invention is to be explained in more detail in the embodiments, without limiting the latter to it.

EXAMPLE 1

1.7 g of the polymer Resomer® RG-756 is dissolved in 29 ml of ethyl acetate and moved into a steel vessel (height 11.5 cm, inside diameter 8 cm). Then, 3 ml of an aqueous 5 mmol tris(hydroxymethyl)aminomethane solution (pH 7.4) that contains 200 mg of human albumin is dispersed with the aid of a mechanical stirrer (Dispermat-FT, VMA-Getzmann GmbH, 5 cm dissolver disk) into the polymer solution for 6 minutes at 10,000 rpm below room temperature. 45 ml of an aqueous solution, consisting of a 2% polyvinyl alcohol solution (molecular weight 9,000–10,000, Aldrich) is added to the W/O-emulsion that is produced while being stirred (8,000 rpm). After a dispersion time of 10 seconds, the W/O/W-emulsion is moved into a 500 ml three-necked flask and stirred using a KPG stirrer. The solvent ethyl acetate is then removed at 20° C. by applying a vacuum (900 mbar), nitrogen, or air feed. After 5 hours, the suspension is washed with 5 l of water or an aqueous solution and concentrated by evaporation in a desired suspension volume. "Cross-flow" filtration is carried out using a Sartocon Mini® (Sartorius AG, Göttingen) Systems. The solvent-free and almost emulsifier-free suspension is mixed with a cryoprotector (for example with a sugar, sugar alcohol, or polyvinyl pyrrolidone derivative), frozen as quickly as possible, for example with liquid nitrogen, and freeze-dried.

The lyophilizate that is resuspended with water or with an aqueous solution contains microcapsules with a human albumin content of 9% (human albumin mass·100/human albumin mass+polymer mass degree of concentration), and they have a diameter of from 0.2 to 8 μm. The encapsulation efficiency is 86%.

EXAMPLE 2

The procedure is the same as in Example 1, whereby 1.7 g of Resomer® RG-756 is not dissolved in 29 ml of ethyl acetate, but rather in 40 ml of methyl acetate.

EXAMPLE 3

The procedure is the same as in Example 1, whereby instead of 1.7 g of the polymer Resomer® RG-756, 1.1 g of the polymer Resomer® RG-858 is used.

EXAMPLE 4

The procedure is the same as in Example 1, whereby instead of 1.7 g of the polymer resomer® RG-756, 3.0 g of the polymer Resomer® RG-858 is used.

EXAMPLE 5

The procedure is the same as in Example 1, whereby instead of a 2% PVA solution, a 2% Brij® 35 solution is used.

EXAMPLE 6

The procedure is the same as in Example 1, whereby instead of a 2% PVA solution, a 2% Brij® 96 solution is used.

EXAMPLE 7

The procedure is the same as in Example 1, whereby instead of a 2% PVA solution, a 2% Tween® 20 solution is used.

EXAMPLE 8

1.1 g of the polymer Resomer® RG-858 is dissolved in 29 ml of ethyl acetate and moved into a steel vessel (height 11.5 cm, inside diameter 8 cm).

Then, 7 ml of a 5 mmol tris(hydroxymethyl) aminomethane solution (pH 7.4) that contains 50 mg of the peptide DesA(2)Nal-beta-Ala-DCpa-DPal-Ser-Tyr-DCit-Leu-Arg-Pro-DAla-NH$_2$ (peptide a) and 2 ml of ethanol is dispersed with the aid of a mechanical stirrer (Dispermat-FT, VMA-Getzmann GmbH, 5 cm dissolver disk) into the polymer solution for 6 minutes at 10,000 rpm below room temperature. 45 ml of an aqueous solution, consisting of a 2% polyvinyl alcohol solution (molecular weight 9,000–10,000, Aldrich) is added to the W/O-emulsion that is produced while being stirred (8,000 rpm). After a dispersion time of 10 seconds, the W/O/W-emulsion is moved into a 500 ml three-necked flask and stirred using a KPG stirrer. The solvent ethyl acetate is then removed at 20° C. by applying a vacuum (900 mbar), nitrogen or air feed. After 5 hours, the suspension is washed with 5 l of water or an aqueous solution and concentrated by evaporation in a desired suspension volume. A "cross-flow" filtration is carried out using a Sartocon Mini® (Sartorius AG, Göttingen) System with a polyolefin membrane (cutoff 0.2 μm). The solvent-free and almost emulsifier-free suspension is mixed with a cryoprotector (for example with a sugar, sugar alcohol or polyvinyl pyrrolidone derivative), frozen as quickly as possible, for example with liquid nitrogen, and freeze-dried.

The lyophilizate that is resuspended with water or with an aqueous solution contains microcapsules with an active ingredient content of 4%. The microcapsules have a diameter of from 0.2 to 8 μm. The encapsulation efficiency is 93%.

EXAMPLE 9

1.1 g of the polymer Resomer® RG-858 is dissolved in 29 ml of ethyl acetate and moved into a steel vessel (height 11.5 cm, inside diameter 8 cm). Then, 5 ml of an aqueous 5 mmol tris(hydroxymethyl)aminomethane solution (pH 7.4) that contains 48 mg of the peptide DesA(2)Nal-Gly-DCpa-DPal-Ser-Tyr-DCit-Leu-Arg-Pro-DAla-NH$_2$ (peptide b) is dispersed with the aid of a mechanical stirrer (Dispermat-FT, VMA-Getzmann GmbH, 5 cm dissolver disk) into the polymer solution for 6 minutes at 10,000 rpm below room temperature. 45 ml of an aqueous solution, consisting of a 2% polyvinyl alcohol solution (molecular weight 9,000–10,000, Aldrich) is added to the W/O-emulsion that is produced while being stirred (8,000 rpm). After a dispersion time of 10 seconds, the W/O/W-emulsion is moved into a 500 ml three-necked flask and stirred using a KPG stirrer. The solvent ethyl acetate is then removed at 20° C. by applying a vacuum (900 mbar), nitrogen or air feed. After 5 hours, the suspension is washed with 5 l of water or an aqueous solution and concentrated by evaporation in a desired suspension volume. The use of a "cross-flow" filtration, for example with a Sartocon Mini® (Sartorius AG, Göttingen) System with a polyolefin membrane (cutoff 0.2 μm), is advantageous. The solvent-free and almost emulsifier-free suspension can be mixed with a cryoprotector (for example with a sugar, sugar alcohol or polyvinyl pyrrolidone derivative) and is frozen as quickly as possible, for example with liquid nitrogen, and freeze-dried.

The lyophilizate that is resuspended with water or with an aqueous solution contains microcapsules with an active ingredient content of 4%. The microcapsules have a diameter of from 0.2 to 8 μm. The encapsulation efficiency is 95.7%.

EXAMPLE 10

1.1 g of the polymer Resomer® RG-858 is dissolved in 30 ml of propyl formate and moved into a steel vessel (height 11.5 cm, inside diameter 8 cm). Then, 5 ml of an aqueous 5 mmol tris(hydroxymethyl)aminomethane solution (pH 7.0) that contains 50 mg of the LHRH antagonist Ac-DNal-DCpa-DPal-Ser-Tyr-DLys (Mor)-Leu-Lys(Mor)Pro-DAla-NH$_2$ (peptide c) is dispersed with the aid of a mechanical stirrer (Dispermat-FT, VMA-Getzmann GmbH, 5 cm dissolver disk) into the polymer solution for 6 minutes at 10,000 rpm below room temperature. 45 ml of an aqueous solution, consisting of a 2% polyvinyl alcohol solution (molecular weight 9,000–10,000, Aldrich), is added to the W/O-emulsion that is produced while being stirred (8,000 rpm). After a dispersion time of 10 seconds, the W/O/W-emulsion is moved into a 500 ml three-necked flask and stirred using a KPG stirrer. The solvent propyl formate is then removed at 20° C. by applying a vacuum (900 mbar), nitrogen or air feed. After 5 hours, the suspension is washed with 5 l of water or an aqueous solution and concentrated by evaporation in a desired suspension volume. A "cross-flow" filtration is carried out with a Sartocon Mini® (Sartorius AG, Göttingen) System with a polyolefin membrane (cutoff 0.2 μm). The solvent-free and almost emulsifier-free suspension is frozen as quickly as possible with liquid nitrogen and freeze-dried.

The lyophilizate that is resuspended with water or with an aqueous solution contains microcapsules with an active ingredient content of 3.9%, and the microcapsules have a diameter of from 0.2 to 8 μm. The encapsulation efficiency is 90.7%.

EXAMPLE 11

1.5 g of the polymer Resomer® RG-858 is dissolved in 30 ml of isopropyl acetate and moved into a steel vessel (height 11.5 cm, inside diameter 8 cm). Then, 5 ml of an aqueous 5 mmol tris(hydroxymethyl)aminomethane solution (pH 7.0) that contains 50 mg of the LHRH antagonist as in Example 10 is dispersed with the aid of a mechanical stirrer (Dispermat-FT, VMA-Getzmann GmbH, 5 cm dissolver disk) into the polymer solution for 6 minutes at 10,000 rpm below room temperature.

45 ml of an aqueous solution, consisting of a 2% polyvinyl alcohol solution (molecular weight 9,000–10,000, Aldrich) is added to the W/O-emulsion that is produced while being stirred (8,000 rpm). After a dispersion time of 10 seconds, the W/O/W-emulsion is moved into a 500 ml three-necked flask and stirred using a KPG stirrer. The solvent isopropyl acetate is then removed at 20° C. by applying a vacuum (900 mbar), nitrogen or air feed. After 5 hours, the suspension is washed with 5 l of water or an aqueous solution and concentrated by evaporation in a desired suspension volume. A "cross-flow" filtration is carried out with a Sartocon Mini® (Sartorius AG, Göttingen) System with a polyolefin membrane (cutoff 0.2 μm), and the solvent-free and almost emulsifier-free suspension is freeze-dried.

The lyophilizate that is resuspended with water or with an aqueous solution contains microcapsules with an active ingredient content of 2.9%, and the microcapsules have a diameter of from 0.2 to 8 μm. The encapsulation efficiency is 90.6%.

EXAMPLE 12

The procedure is the same as in Example 1, whereby the 5 mmol tris(hydroxymethyl)aminomethane solution (pH 7.0) is replaced by a 5 mmol phosphate buffer solution (PBS, pH 7.2).

EXAMPLE 13

The procedure is the same as in Example 1, whereby instead of 200 mg of HSA that is dissolved in 3 ml of tris-buffer (pH=7.4), 750 mg of HSA that is dissolved in 5 ml of tris-buffer (pH=7.4) is used.

The lyophilizate that is resuspended in water or aqueous solutions contains microcapsules with an HSA content of 30%. The encapsulation efficiency is 90.9%.

EXAMPLE 14

The procedure is the same as in Example 13, whereby instead of 2% polyvinyl alcohol solution, a 2% Poloxamer F 127 solution is used.

EXAMPLE 15

The procedure is the same as in Example 13, whereby instead of 2% polyvinyl alcohol solution, a 2% Poloxamine T 707 solution is used.

EXAMPLE 16

The procedure is the same as in Example 13, whereby instead of 2% polyvinyl alcohol solution, a 2% Poloxamine T 908 solution is used.

EXAMPLE 17

The procedure is the same as in Example 1, whereby 200 mg of HSA is replaced by 200 mg of insulin (human, recombinant (pfs), Sigma Chemie [Sigma Chemistry] No. I 0259).

EXAMPLE 18

The procedure is the same as in Example 1, whereby 200 mg of HSA is replaced by 200 mg of interferon (human leukocyte (pfs) (α-IFH, Le), Sigma Chemie No. I 1008).

EXAMPLE 19

The procedure is the same as in Example 1, whereby 200 mg of HSA is replaced by 200 mg of insulin (human, gamma (pfs) (γ-IFN), Sigma Chemie No. I 6507).

What is claimed is:

1. A process for the production of morphologically uniform microcapsules that comprise biodegradable polymers or copolymers and contain at least one peptide, protein or other water-soluble, biologically active substance as the active ingredient, by an induced phase transition process which comprises:
   (a) dissolving a polymer selected from the group consisting of polyamides, polyanhydrides, polyorthoesters, polyacetates, polylactones, polyorthocarbonates, polyesters, and polyesters of hydroxycarboxylic acids or block copolymers of polyesters of hydroxycarboxylic acids and polyethylene glycol, in a halogen-free solvent that is partially water-miscible;
   (b) dispersing therein a solution of the active ingredient to form a W/O emulsion;
   (c) adding an aqueous solution that contains a surfactant or a mixture of surfactants to this W/O emulsion wherein the surfactant solution is present in an amount less than 60% v/v;
   (d) removing the solvent, thus forming the microcapsules; and
   (e) optionally, removing residual solvent, unencapsulated active ingredient and/or surfactant.

2. The process according to claim 1 wherein the haolgen-free solvent is selected from the group consisting of acetone, ethanol, $C_1$–$C_4$ alkyl formates, $C_1$–$C_4$ alkyl lactates and mixtures thereof.

3. The process according to claim 1, wherein the halogen-free solvent is selected from the group consisting of methyl acetate, ethyl acetate, isopropyl acetate and propyl formate.

4. The process according to claim 1, wherein the polymer is a (DL-lactide-coglycolide)-polymer.

5. The process according to claim 1, wherein the active ingredient is selected from the group consisting of human serum albumin, a peptide, a protein, interferon, betaferon beta-1b, insulin and an LHRH antagonists or analog thereof.

6. The process according to claim 1, wherein at least one active ingredient is selected from the group consisting of:
   (a) DesA(2) Nal-beta Ala-Dcpa-Dpal-Ser-Tyr-Dcit-Leu-Arg-pro-Dala-$NH_2$,
   (b) DesA(2)Nal-Gly-Dcpa-Dpal-Ser-Tyr-Dcit-Leu-Arg-Pro-Dala-$NH_2$,
   (c) Ac-Dnal-Dcpa-Dpal-Ser-Tyr-Dlys(Mor)-Leu-Lys(Mor)Pro-Dala-$NH_2$.

7. The process according to claim 1, wherein the removal of the residual solvent, unencapsulated active ingredient and/or surfactant, optionally adhering to the particle surface, is carried out by cross-flow filtration.

8. Morphologically uniform microcapsules with a degree of concentration of between 3 to 30% by weight and a diameter of 200 μm to 500 μm produced according to the process of claim 1.

9. Microcapsules according to claim 8, with a diameter of between 0.2 to 8 μm.

10. The process of claim 1, wherein the process results in an encapsulation efficiency of at least 85%.

11. The process according to claim 1, further comprising adding a cryoprotector to the microcapsules and freeze-drying.

12. The process of claim 1, wherein the polymer is selected from the group consisting of polyglycolides, copolymer of glycolides, L-polylactides, stereocopolymers of L-polylactides, copolymers of L-polylactides, poly-β-hydroxypropionate, poly-p-dioxanone, poly-δ-valerolactone, hydrophobized polysaccharides, hyaluronic acid, dextrans, hydrophobized amylopectin, poly-ε-caprolactone, AB-block copolymers of L-polylactides (PLA) and star-polyethylene glycol (PEG), ABA-triblock copolymers of PLA-PEG-PLA, S (3)-PEG-PLA block copolymers and S (4)-PEG-PLA block copolymers.

13. A process according to claim 1, wherein the active ingredient solution is provided with a buffer to maintain a pH between 6.0 and 8.0

14. The process according to claim 13, wherein the buffered solution is selected from the group consisting of a phosphate buffer solution, a citrate buffer solution and a tris(hydroxymethyl)aminomethane solution.

\* \* \* \* \*